US012623058B2

(12) United States Patent
Burkholz

(10) Patent No.: US 12,623,058 B2
(45) Date of Patent: May 12, 2026

(54) INTEGRATED CATHETER WITH STABILIZED NEAR-PATIENT PORT EXTENSION SET ARCHITECTURE

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 686 days.

(21) Appl. No.: 17/994,955

(22) Filed: Nov. 28, 2022

(65) Prior Publication Data

US 2023/0166086 A1     Jun. 1, 2023

Related U.S. Application Data

(60) Provisional application No. 63/284,129, filed on Nov. 30, 2021.

(51) Int. Cl.
| | |
|---|---|
| *A61M 25/02* | (2006.01) |
| *A61B 5/15* | (2006.01) |
| *A61B 5/153* | (2006.01) |
| *A61M 25/00* | (2006.01) |
| *A61M 25/06* | (2006.01) |
| *A61M 39/10* | (2006.01) |

(52) U.S. Cl.
CPC ..... *A61M 25/0606* (2013.01); *A61B 5/15003* (2013.01); *A61B 5/150206* (2013.01); *A61B 5/153* (2013.01); *A61M 25/0021* (2013.01); *A61M 25/0043* (2013.01); *A61M 25/0097* (2013.01); *A61M 25/02* (2013.01); *A61M 25/06* (2013.01); *A61M 39/105* (2013.01);

*A61M 2025/0266* (2013.01); *A61M 39/10* (2013.01); *A61M 2039/1077* (2013.01)

(58) Field of Classification Search
CPC .......... A61M 25/0021; A61M 25/0043; A61M 25/0097; A61M 25/02; A61M 25/06; A61M 25/0606; A61M 39/10; A61M 39/105; A61M 2025/0266; A61M 2039/1077; A61B 5/15003; A61B 5/150206; A61B 5/153
See application file for complete search history.

(56) References Cited

U.S. PATENT DOCUMENTS

| | | | |
|---|---|---|---|
| 11,090,461 | B2 | 8/2021 | Ehrenreich et al. |
| 2006/0270994 | A1 | 11/2006 | Bierman |
| 2015/0224285 | A1 | 8/2015 | Howell et al. |
| 2019/0160275 | A1 | 5/2019 | Funk et al. |
| 2020/0230353 | A1 | 7/2020 | Burkholz et al. |
| 2021/0212618 | A1 | 7/2021 | Burkholz et al. |

OTHER PUBLICATIONS

B Braun. STEADYCare Extension Set with Wedge Catheter Stabilizer, 2021, <https://www.bbraunusa.com/en/products/b4/steadycare-extensionsetwithwedgecatheterstabilizer.html>.

*Primary Examiner* — John Kim
(74) *Attorney, Agent, or Firm* — The Webb Law Firm

(57) ABSTRACT

An integrated catheter includes a catheter adapter having a catheter and an inlet, the catheter configured to be inserted into a patient's vasculature. The integrated catheter also includes a near-patient access port having a first port at a first end and a female luer connector at a second end, as well as intermediate tubing extending between the inlet of the catheter adapter and the first port of the near-patient access port. Additionally, the integrated catheter includes a stabilization platform configured to stabilize at least the near-patient access port on a patient's skin.

15 Claims, 12 Drawing Sheets

INTEGRATED CATHETER WITH STABILIZED NEAR-PATIENT PORT EXTENSION SET ARCHITECTURE

CROSS-REFERENCE TO RELATED APPLICATION

The present application claims priority to U.S. Provisional Patent Application Ser. No. 63/284,129, entitled "Integrated Catheter with Stabilized Near-Patient Port Extension Set Architecture", filed Nov. 30, 2021, the entire disclosure of which is hereby incorporated by reference in its' entirety.

BACKGROUND OF THE INVENTION

Field of the Invention

The present disclosure relates to an integrated catheter having a stabilized near-patient access port extension set architecture configured for use with a blood draw device.

Description of Related Art

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter ("PIVC"). The over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from a skin surface of the patient. The catheter and introducer needle are generally inserted at a shallow angle through the skin into the vasculature of the patient. In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period.

Accordingly, blood draw devices have been developed to collect blood samples through an existing PIVC. Blood draw devices attach to the PIVC and include a flexible flow tube that is advanced through the PIVC, beyond the catheter tip, and into a vessel to collect a blood sample. After blood collection, the blood draw device is removed from the PIVC and discarded. One example of such a blood draw device, known as PIVO™ from Velano Vascular, Inc., is shown and described in U.S. Pat. No. 11,090,461, which is hereby incorporated by reference in its entirety.

As described in U.S. Pat. No. 11,090,461, the blood draw device includes an introducer having an actuator slidably coupled thereto, with the actuator being configured to selectively advance the flexible flow tube through the PIVC. The introducer is couplable to, e.g., an integrated needle free connector (NFC) of a near-patient access port by way of a lock positioned on a distal end portion of the introducer. However, in certain circumstances, undesirable movement and/or angulation of the near-patient access port or associated tubing may adversely affect the smooth advancement (or retraction) of the flexible flow tube and/or the collection of blood through the flexible flow tube of the blood draw device. Furthermore, the use of an integrated (i.e., non-removable) needle free connector may complicate the flushing of the near-patient access port after a blood draw procedure.

SUMMARY OF THE INVENTION

Accordingly, there is a need to provide an integrated catheter coupled to a stabilized near-patient access port for improved blood draw via, e.g., a PIVO™ blood draw device. Additionally, there is a need for a system utilizing a removable NFC for improved flushing characteristics of the near-patent access port.

In accordance with an aspect of the present disclosure, an integrated catheter is disclosed. The integrated catheter includes a catheter adapter having a catheter and an inlet, the catheter configured to be inserted into a patient's vasculature, and a near-patient access port having a first port at a first end and a female luer connector at a second end. The integrated catheter also includes intermediate tubing extending between the inlet of the catheter adapter and the first port of the near-patient access port, and a stabilization platform configured to stabilize at least the near-patient access port on a patient's skin.

In some embodiments, the near-patient access port further includes a side port extending therefrom.

In some embodiments, the side port extends 90° relative to an axis of the first port and the female luer connector of the near-patient access port.

In some embodiments, the integrated catheter further includes extension tubing extending from the side port of the near-patient access port.

In some embodiment, the integrated catheter further includes a medical component positioned at an end of the extension tubing.

In some embodiments, the integrated catheter further includes a needle free connector couplable to the female luer connector of the near-patient access port.

In some embodiments, the needle free connector is removably couplable to the female luer connector.

In some embodiments, the stabilization platform is coupled to the needle free connector.

In some embodiments, the stabilization platform is integrally formed with the needle free connector.

In some embodiments, the integrated catheter further includes a t-extension set removably couplable to the female luer connector of the near-patient access port.

In some embodiments, the t-extension set includes a side port coupled to a second extension tube, wherein the second extension tube is coupled to a second medical component.

In some embodiments, the stabilization platform is coupled to the t-extension set.

In some embodiments, the stabilization platform is integrally formed with the t-extension set.

In some embodiments, the stabilization platform is coupled to the near-patient access port.

In some embodiments, the stabilization platform is integrally formed with the near-patient access port.

In some embodiments, the stabilization platform comprises opposing first and second stabilizing wings.

In accordance with another aspect of the present disclosure, an integrated catheter is disclosed having a catheter adapter including a catheter and an inlet, the catheter configured to be inserted into a patient's vasculature, as well as a near-patient access port having a first port at a first end and a female luer connector at a second end. The integrated catheter further includes intermediate tubing extending between the inlet of the catheter adapter and the first port of the near-patient access port, and a stabilization platform configured to stabilize at least the near-patient access port on a patient's skin, wherein the stabilization platform is positioned on the near-patient access port.

In some embodiments, the stabilization platform is formed separately from the near-patient access port.

In accordance with another aspect of the present disclosure, an integrated catheter is disclosed having a catheter adapter including a catheter and an inlet, the catheter configured to be inserted into a patient's vasculature, as well as a near-patient access port having a first port at a first end and a female luer connector at a second end. The integrated catheter further includes intermediate tubing extending between the inlet of the catheter adapter and the first port of the near-patient access port, a needle free connector coupled to the female luer connector of the near-patient access port, and a stabilization platform configured to stabilize at least the needle free connector on a patient's skin, wherein the stabilization platform is positioned on needle free connector.

In some embodiments, the needle free connector and the stabilization platform are removable from the female luer connector of the near-patient access port.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Figure 1:
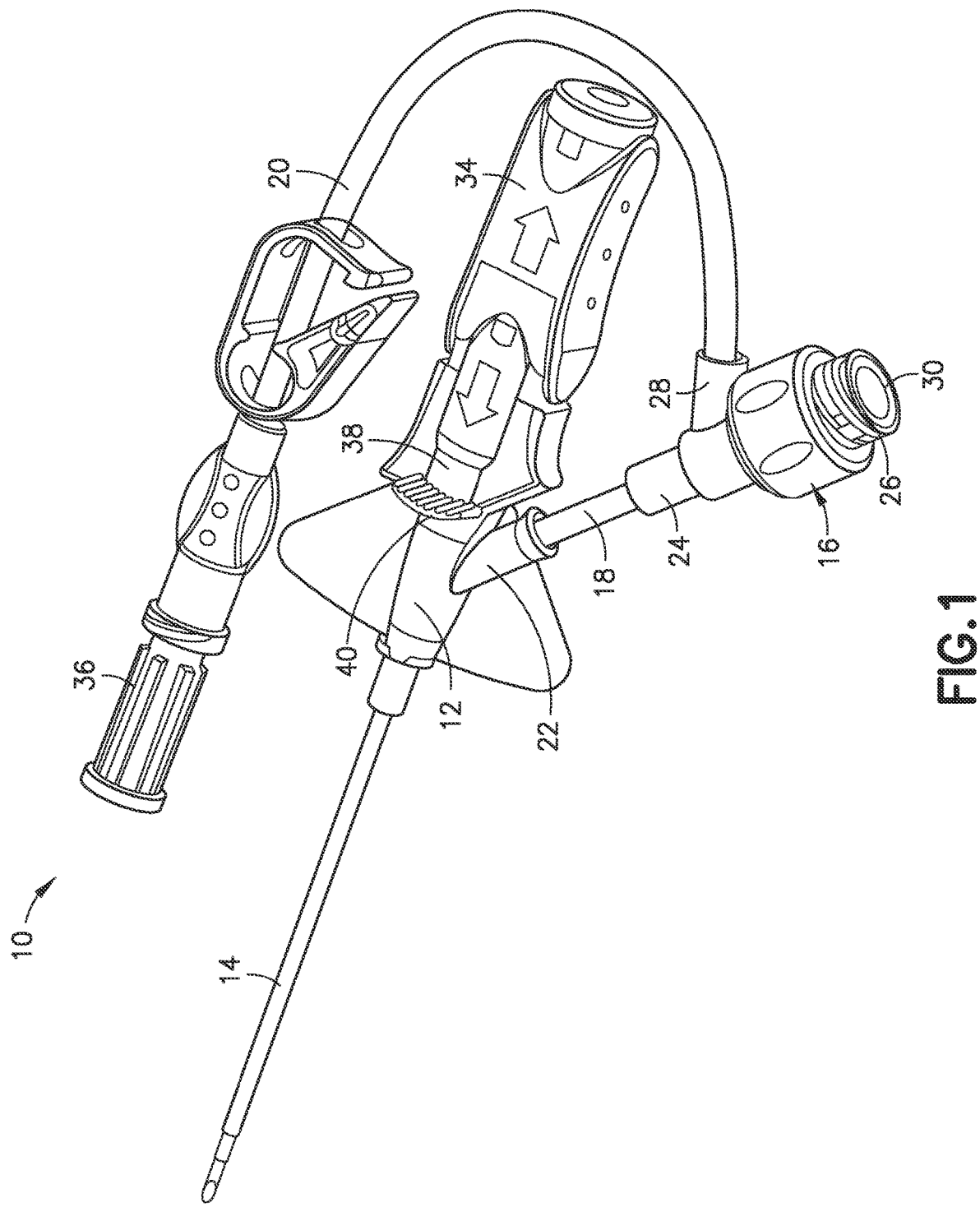
FIG. 1 is a perspective view of an integrated intravenous catheter in accordance with an aspect of the present disclosure.

Spatial or directional terms, such as "left", "right", "inner", "outer", "above", "below", and the like, are not to be considered as limiting as the invention can assume various alternative orientations.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less.

The terms "first", "second", and the like are not intended to refer to any particular order or chronology, but refer to different conditions, properties, or elements.

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

Referring to FIG. 1, an integrated intravenous catheter 10 in accordance with an aspect of the present disclosure is shown. The integrated intravenous catheter 10 includes a catheter adapter 12 having a catheter 14 configured to be inserted into a patient's vasculature, a near-patient access port 16, intermediate tubing 18, and extension tubing 20. The catheter adapter 12 includes an inlet 22. In some embodiments, the catheter adapter 12 may include a stabilization feature. Alternatively, in other embodiments, the catheter adapter 12 may be provided without stabilization.

In the embodiment shown in FIG. 1, the near-patient access port 16 includes a first port 24, a second port 26 positioned opposite the first port 24, and a side port 28 positioned between the first port 24 and the second port 26. In some embodiments, the second port 26 may include a valve member 30. Furthermore, in some embodiments, the near-patient access port 16 includes an integrated (i.e., non-removable) needle free connector. While near-patient access port 16 is shown as forming a y-adapter, it is to be understood that near-patient access port 16 may be configured as a t-adapter.

The intermediate tubing 18 extends between the inlet 22 of the catheter adapter 12 and the first port 24 of the near-patient access port 16. The extension tubing 20 extends from the side port 28 of the near-patient access port 16. The intermediate tubing 18 is configured to provide flexibility when inserting and dressing the catheter 14 and also when manipulating the near-patient access port 16 for flushing, blood draw, and/or other procedure without disturbing the catheter insertion site.

Referring still to FIG. 1, in some embodiments, the integrated catheter 10 includes a needle hub assembly 34 and a medical component 36, such as, e.g., a vent plug, with the medical component 36 coupled to the side port 28 of the needle free connector 16 via the extension tubing 20. The needle hub assembly 34 is assembled with the catheter adapter 12 by inserting a needle (not shown) into a lumen of the catheter 14. In one aspect or embodiment, the needle hub assembly 34 includes a needle shield 38 configured to secure a tip of the needle within the needle shield 38 after use. The needle shield 38 may be activated passively. The needle hub assembly 34 includes a push tab 40 to facilitate catheter advancement during insertion. The push tab 40 also allows for one-handed or two-handed advancement. In one aspect or embodiment, the catheter adapter 12 includes one or more wings, as shown, configured to engage a skin surface of a patient. In another aspect or embodiment, the catheter adapter 12 does not include wings.

In some embodiments, at least a portion of the near-patient access port 16 is transparent. The connector components of the integrated catheter 10 may be transparent, opaque, and/or colored. In one aspect or embodiment, the near-patient access port 16 includes an anti-reflux valve.

In some embodiments, the medical component 36 at the end of the extension tubing 20 is a single port or dual port connector and may include a variety of connectors, including needle free connectors or needle access connectors, such as a PRN. The extension tubing 20 may be left or right facing. In some embodiments, in addition to a vent plug, the medical component 36 may be a removable or non-removable needle free connector or needle access connectors, such as a PRN, that is attached to a female luer connection provided on the extension tubing 20. In some embodiments, a dual female luer port may be bonded or otherwise attached to the extension tubing 20 instead of a single luer connector.

Figure 2:
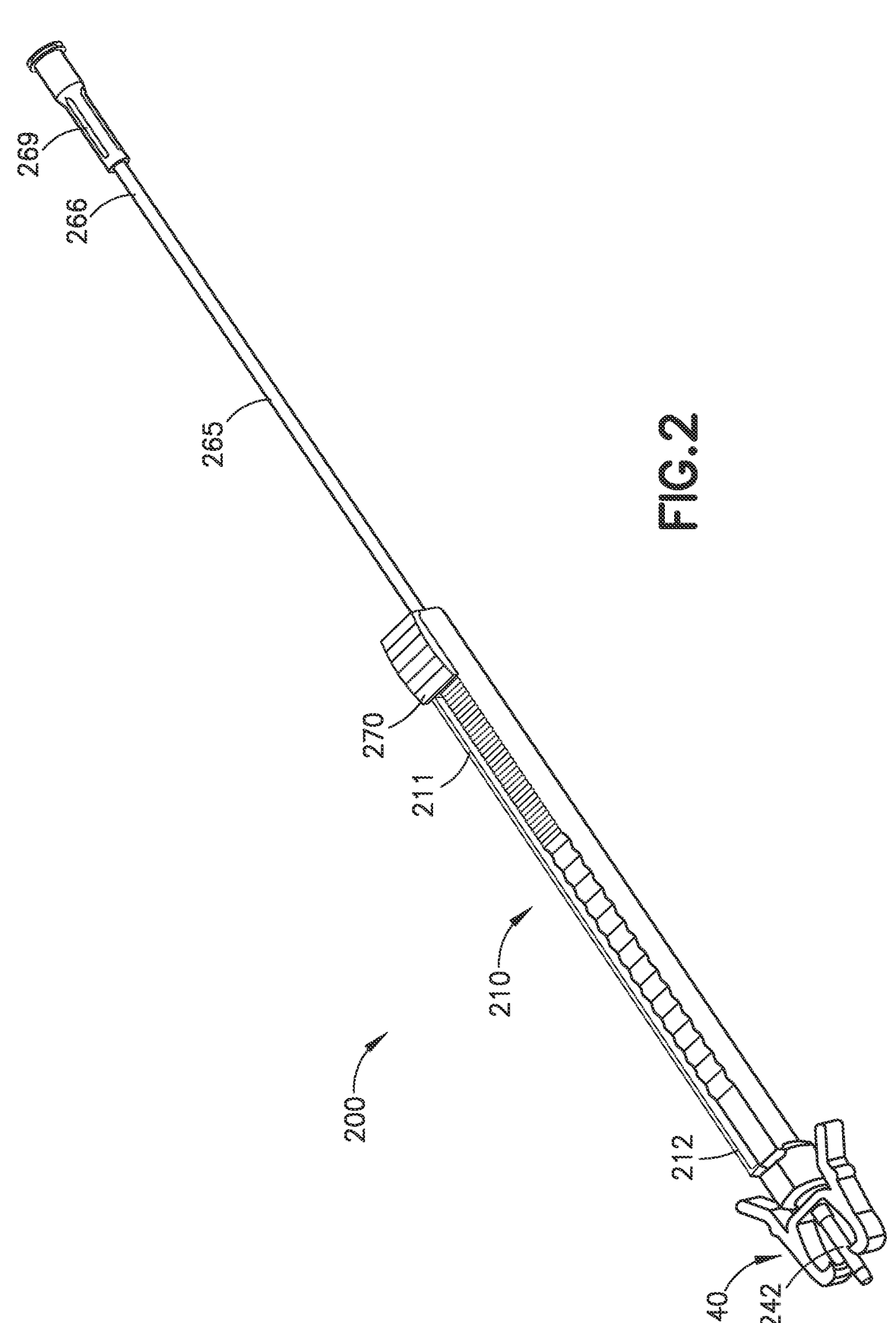
FIG. 2 is a perspective view of a blood draw device configured for use with the integrated intravenous catheter of FIG. 1.

Next, referring to FIG. 2, a blood draw device 200 in accordance with an aspect of the present disclosure is illustrated. The blood draw device 200 may be, e.g., the PIVO™ blood draw device commercially available from Velano Vascular, Inc. In one aspect or embodiment, the blood draw device 200 is the same or similar to the blood draw device shown in U.S. Pat. No. 11,090,461, which is hereby incorporated by reference in its entirety. In one aspect or embodiment, the blood draw device 200 may be any device that advances tubing, a probe, a guidewire, instrument, and/or sensor into the fluid path of the integrated intravenous catheter 10 or beyond the tip of the catheter 14.

Blood draw device 200 may include an introducer 210, a lock 240, a secondary catheter 265, and an actuator 270. The introducer includes a proximal end portion 211 and a distal end portion 212, with the lock 240 being located adjacent the distal end portion 212. The secondary catheter 265 includes the proximal end portion 266 which is coupled to and/or otherwise includes a coupler 269. The coupler 269 is configured to physically and fluidically couple the secondary catheter 265 to any suitable device such as, for example, a fluid reservoir, fluid source, syringe, evacuated container holder (e.g., having a sheathed needle or configured to be coupled to a sheathed needle), pump, and/or the like.

In accordance with some embodiments, a user may manipulate the blood draw device 200 to couple the lock 240 to, e.g., the catheter adapter 12 of integrated intravenous catheter 10. For example, in some embodiments, the user can exert a force sufficient to pivot the first and second clip arms of the lock 240 such that a portion of the catheter adapter 12 can be inserted into the space defined between the arms of the lock 240 and, for example, a nose 242 extending distally from the lock 240. In some embodiments, the nose 242 can be inserted into, e.g., the near-patient access port 16 of the catheter adapter 12 when the lock 240 is coupled thereto, while the first and second clip arms of the lock 240 may latch onto an exterior surface (or surfaces) of the near-patient access port 16 to hold the blood draw device 200 in place relative to the catheter adapter 12. The proximity of the near-patient access port 16 enables the flexible flow tube of the blood draw device 200 to protrude a sufficient distance beyond the tip of catheter 14 when the flexible flow tube is in an extended configuration.

Figure 3A:
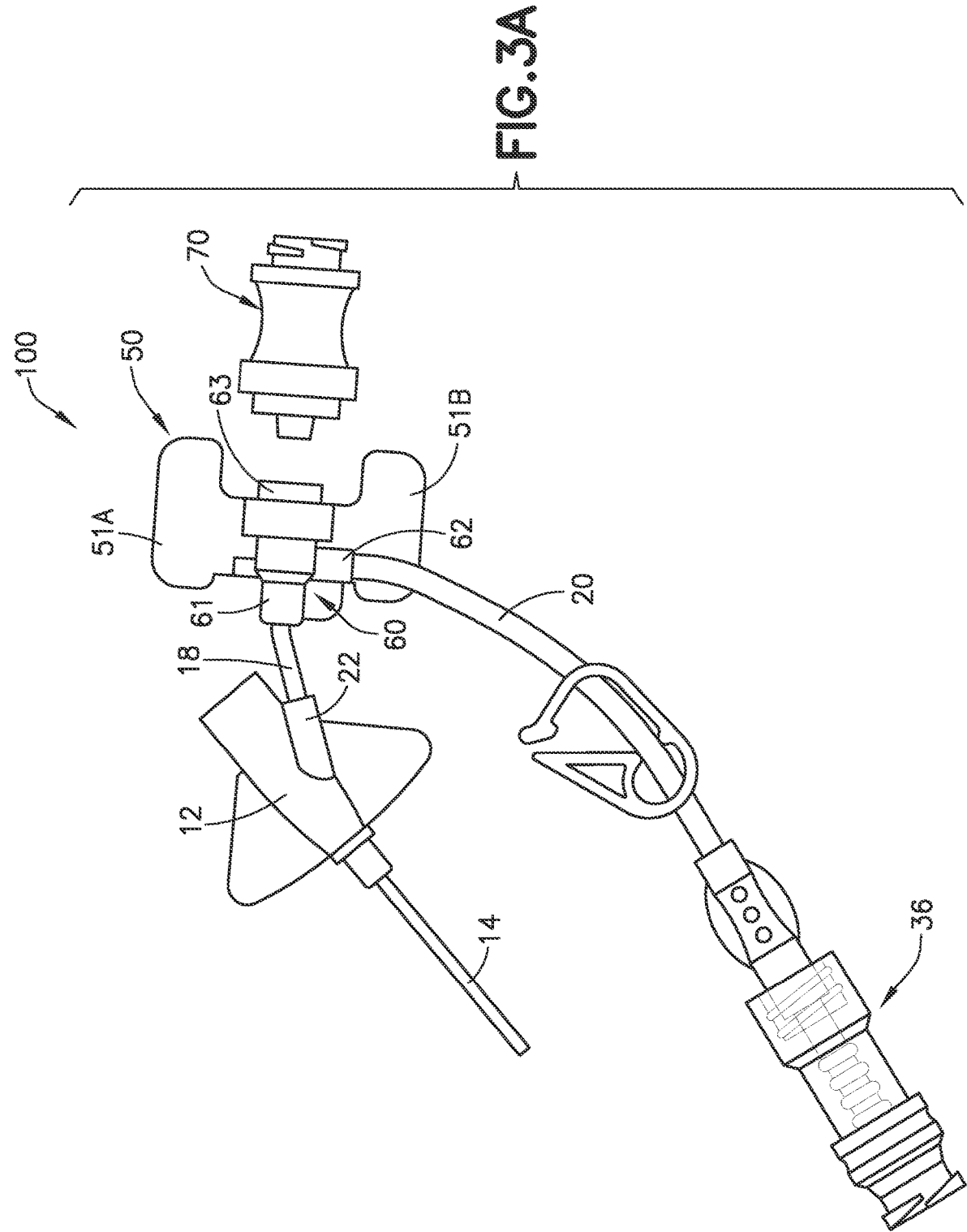
FIG. 3A is a top plan view of an integrated catheter configuration in a partially disassembled configuration in accordance with an aspect of the present disclosure.
Figure 3B:
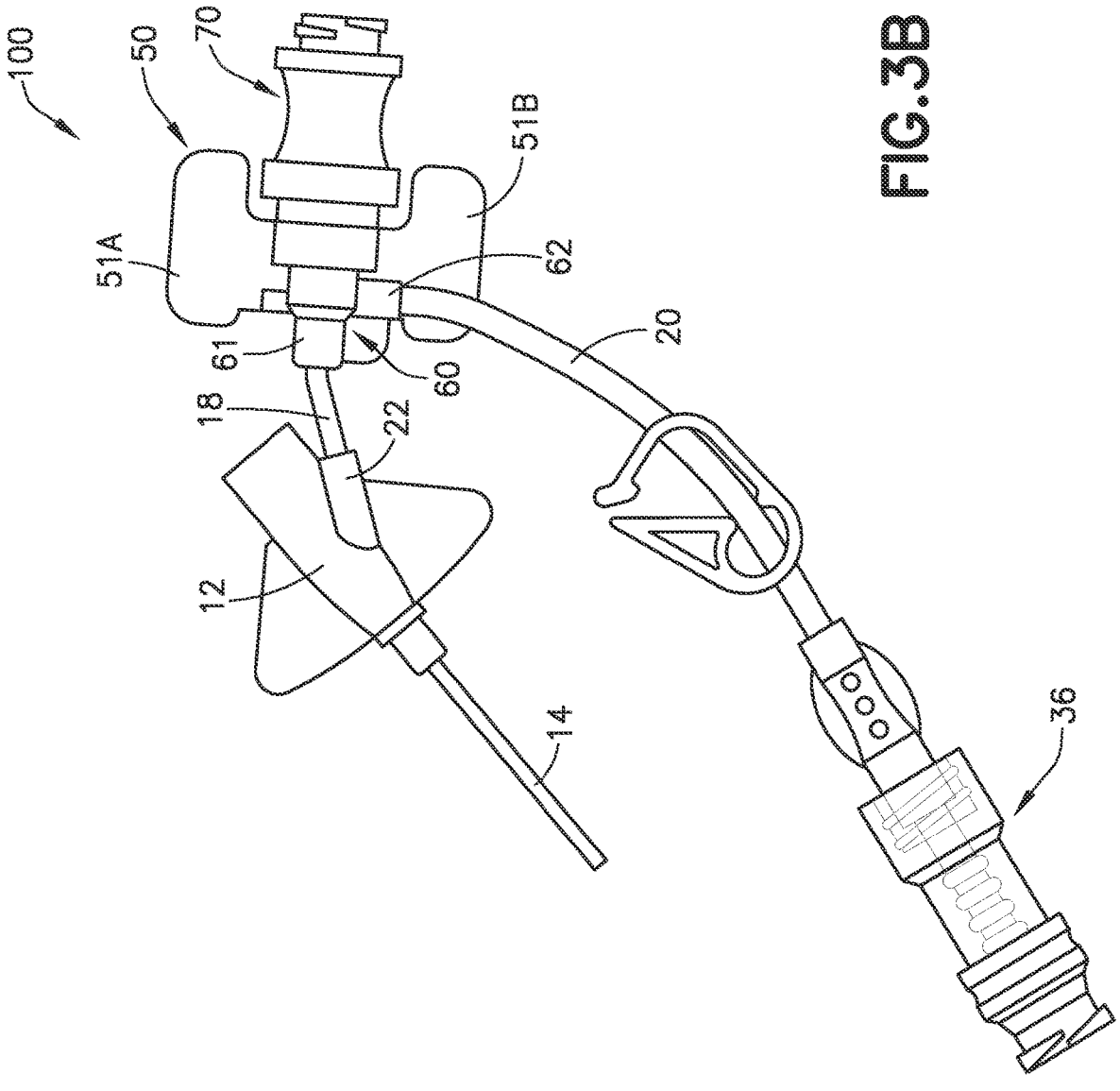
FIG. 3B is a top plan view of the integrated catheter configuration of FIG. 3A in an assembled configuration.

Next, referring to FIGS. 3A and 3B, an integrated catheter configuration 100 in accordance with an aspect of the present disclosure is shown. The integrated catheter configuration 100 includes a near-patient access port 60 configured as a t-adapter (i.e., a 90° adapter), with a first port 61 coupled to the intermediate tubing 18 and a side port 62 extending substantially perpendicular to the first port 61 and configured to be coupled to, e.g., the extension tubing 20. The near-patient access port 60 further includes a female luer connector 63, with the female luer connector 63 being couplable to, e.g., a removable needle free connector (NFC) 70. In other embodiments, the needle free connector 70 may be integrated (i.e., non-removable) with the near-patient access port 60. Furthermore, it is to be understood that near-patient access port 60 is not limited to a t-adapter configuration, and may instead be formed as a y-adapter (i.e., a 30°-150° adapter). The needle free connector 70 may be utilized as a connection interface between the near-patient access port 60 and, e.g., a blood draw device such as blood draw device 200 described above with respect to FIG. 2.

Referring still to FIGS. 3A and 3B, the integrated catheter configuration 100 also includes a stabilization platform 50. In some embodiments, stabilization platform 50 is formed separately from, and may be attached or coupled to, the near-patient access port 60. However, in other embodiments, the stabilization platform 50 may be integrally formed with the near-patient access port 60. In some embodiments, stabilization platform 50 includes opposing stabilizing wings 51A, 51B, which may act provide improved securement and stability of the near-patient access port 60 on the patient's skin. Such a configuration may improve the success of blood draw device compatibility and access with the integrated catheter, as well as reduce the risk of catheter and/or blood draw device complications (such as, e.g., flow tube kinking, etc.) due to device manipulation during access with the integrated catheter. Additionally and/or alternatively, the stabilization platform 50 may help to avoid patient skin irritation due to movement of the near-patient access port 60.

Furthermore, because the needle free connector 70 may be removable from the near-patient access port 60, flushing of the near-patient access port 60 via, e.g., the medical component 36 at the end of the extension tubing 20 may be improved.

Stabilization platform 50 may be fully rigid, rigid with some flexibility, semi-rigid, semi-rigid with one or more flexibility hinges, soft, or soft with flexibility features. Additionally, in some embodiments, stabilization platform 50 may be angled and the female luer connector 63 and/or the needle free connector 70 may be raised to provide a substantially unrestricted pathway for advancement of the flexible flow tube of the blood draw device. Additionally, the stabilization platform 50 and/or stabilizing wings 51A, 51B may have a substantially flat bottom, a curved bottom, or a partially curved bottom.

As noted above, in some embodiments, the stabilization platform 50 may be formed separately from the near-patient access port 60, and may be attached, bonded, and/or coupled to the near-patient access port 60 via any appropriate method. Alternatively, in other embodiments, the stabilization platform 50 may be attached, bonded, and/or coupled to the needle free connector 70. Alternatively, the stabilization platform 50 may be integrally molded or formed as part of the near-patient access port 60 or the needle free connector 70.

Figure 4A:
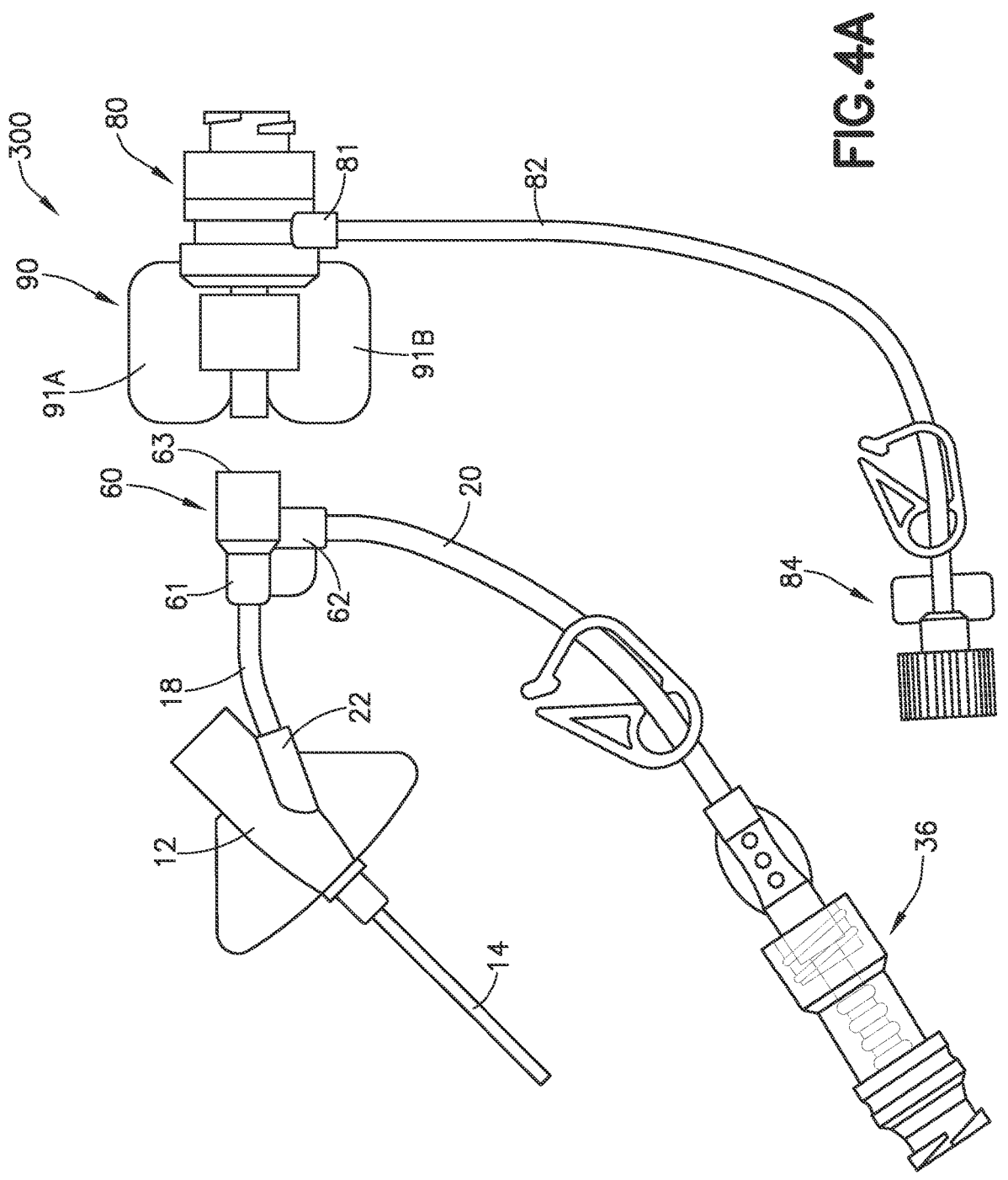
FIG. 4A is a top plan view of an integrated catheter configuration in a partially disassembled configuration in accordance with another aspect of the present disclosure.
Figure 4B:
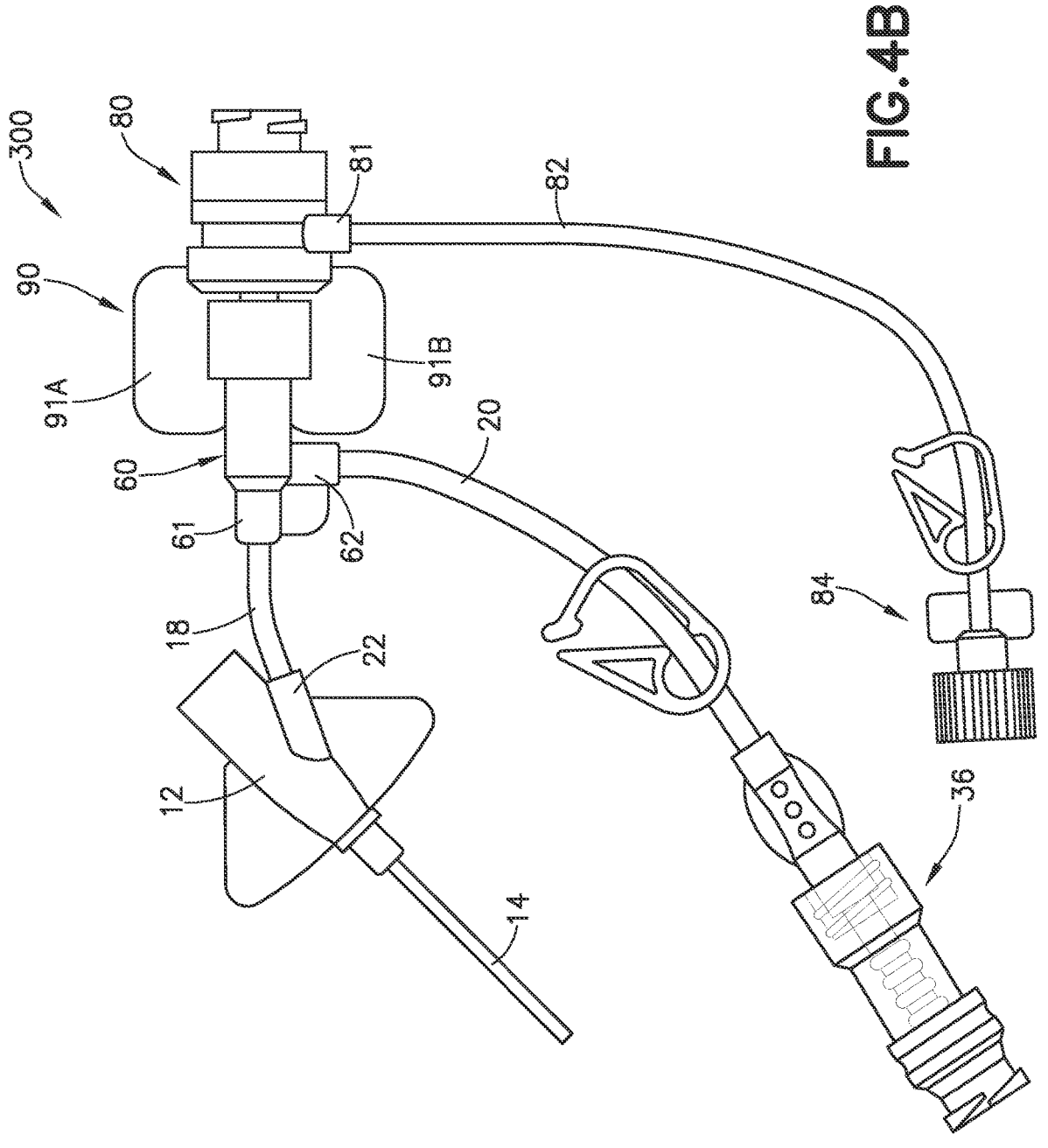
FIG. 4B is a top plan view of the integrated catheter configuration of FIG. 4A in an assembled configuration.

Next, referring to FIGS. 4A and 4B, an integrated catheter configuration 300 in accordance with another aspect of the present disclosure is shown. The integrated catheter configuration 300 includes the near-patient access port 60 configured as a t-adapter (i.e., a 90° adapter) as described above with respect to FIGS. 3A and 3B, with the first port 61 coupled to the intermediate tubing 18 and the side port 62 extending substantially perpendicular to the first port 61 and configured to be coupled to, e.g., the extension tubing 20. The near-patient access port 60 further includes the female luer connector 63.

However, unlike integrated catheter configuration 100 described above with respect to FIGS. 3A and 3B, which included a stabilization platform 50 integrated with or coupled to the near-patient access port 60, the integrated catheter configuration 300 of FIGS. 4A and 4B includes a removable t-extension set 80, wherein the t-extension set 80 incorporates a stabilization platform 90. In the embodiment shown in FIGS. 4A and 4B, the t-extension set 80 is configured as a needle free connector removably couplable to the female luer connector 63 of the near-patient access port 60. The t-extension set 80 includes a side port 81 couplable to extension tubing 82, with the extension tubing 82 couplable to a second medical component 84, such as, e.g., a vent plug. Alternatively, in other embodiments, it is to be understood that the t-extension set 80 may be integrated (i.e., non-removable) with the near-patient access port 60. Furthermore, it is to be understood that t-extension set 80 is not limited to a t-adapter configuration, and may instead be formed as a y-adapter (i.e., a 30°-150° adapter). The t-extension set 80 may be utilized as a connection interface between the near-patient access port 60 and, e.g., a blood draw device such as blood draw device 200 described above with respect to FIG. 2.

As noted above, the stabilization platform 90 is associated with the t-extension set 80, not the near-patient access port 60. In some embodiments, stabilization platform 90 is formed separately from, and may be attached or coupled to, the t-extension set 80. However, in other embodiments, the stabilization platform 90 may be integrally formed with the t-extension set 80.

In some embodiments, stabilization platform 90 includes opposing stabilizing wings 91A, 91B, which may act provide improved securement and stability of the t-extension set 80 (as well as the near-patient access port 60) on the patient's skin. Such a configuration may improve the success of blood draw device compatibility and access with the integrated catheter, as well as reduce the risk of catheter and/or blood draw device complications (such as, e.g., flow tube kinking, etc.) due to device manipulation during access with the integrated catheter. Additionally and/or alternatively, the stabilization platform 90 may help to avoid patient skin irritation due to movement of the t-extension set 80.

Furthermore, because the t-extension set 80 may be removable from the near-patient access port 60, flushing of the near-patient access port 60 via, e.g., the medical component 36 at the end of the extension tubing 20 may be improved.

Stabilization platform 90 may be fully rigid, rigid with some flexibility, semi-rigid, semi-rigid with one or more flexibility hinges, soft, or soft with flexibility features. Additionally, in some embodiments, stabilization platform 90 may be angled and the female luer connector 63 and/or the t-extension set 80 may be raised to provide a substantially unrestricted pathway for advancement of the flexible flow tube of the blood draw device. Additionally, the stabilization platform 90 and/or stabilizing wings 91A, 91B may have a substantially flat bottom, a curved bottom, or a partially curved bottom.

As noted above, in some embodiments, the stabilization platform 90 may be formed separately from the t-extension set 80, and may be attached, bonded, and/or coupled to the t-extension set 80 via any appropriate method. Alternatively, the stabilization platform 90 may be integrally molded or formed as part of the t-extension set 80.

Figure 5A:
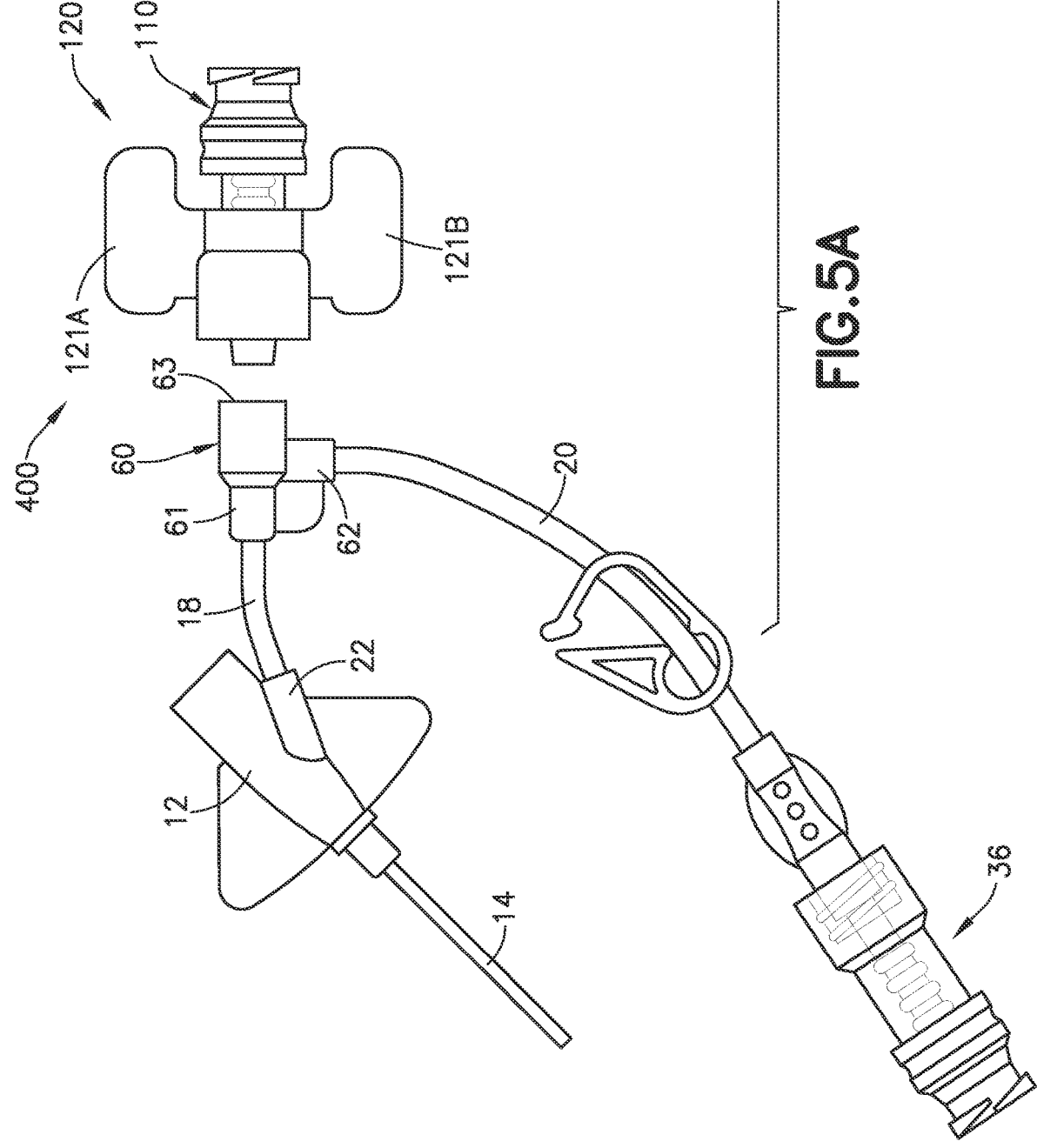
FIG. 5A is a top plan view of an integrated catheter configuration in a partially disassembled configuration in accordance with another aspect of the present disclosure.
Figure 5B:
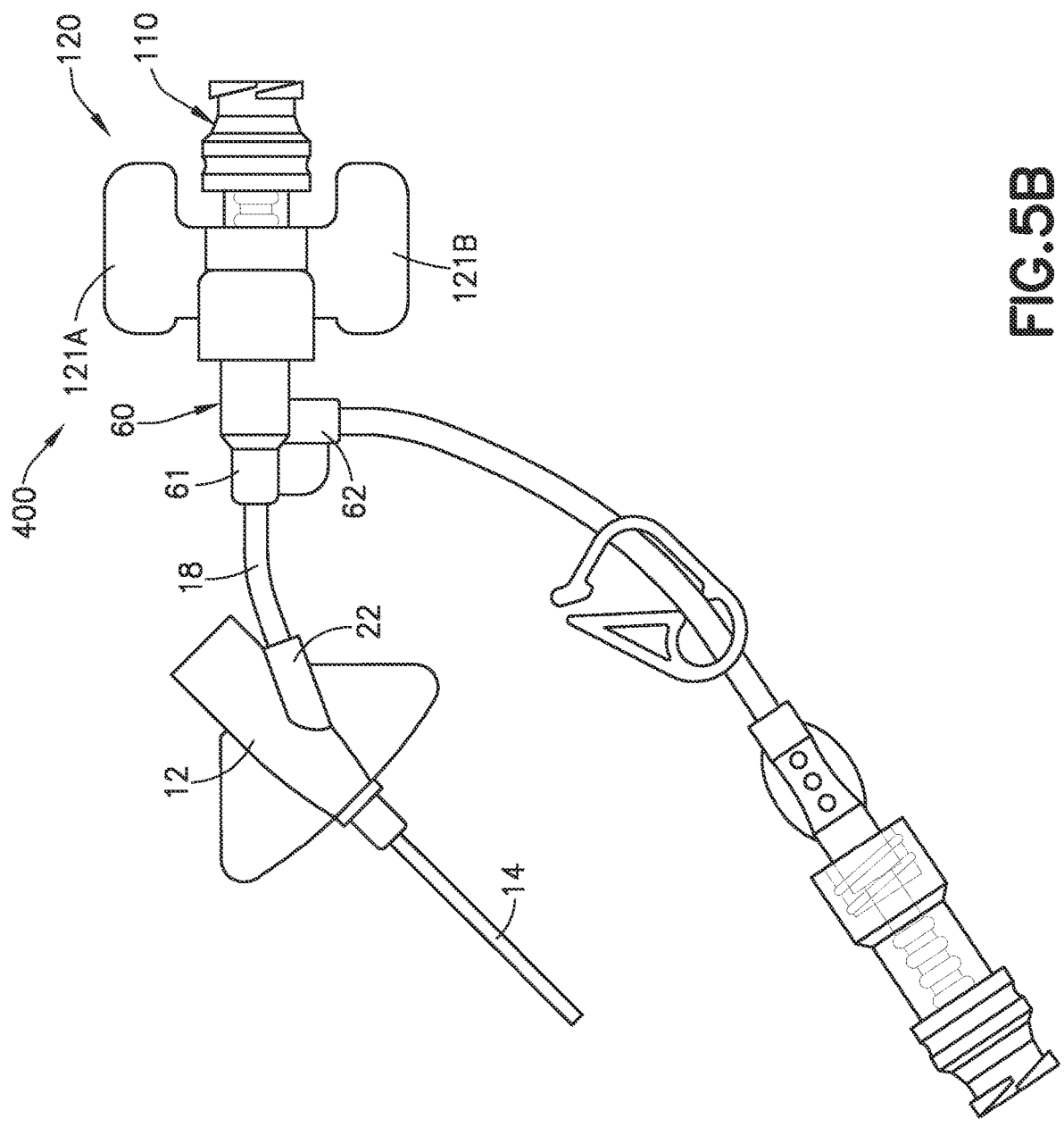
FIG. 5B is a top plan view of the integrated catheter configuration of FIG. 5A in an assembled configuration.

Next, referring to FIGS. 5A and 5B, an integrated catheter configuration 400 in accordance with another aspect of the present disclosure is shown. The integrated catheter configuration 400 includes the near-patient access port 60 configured as a t-adapter (i.e., a 90° adapter) as described above with respect to FIGS. 3A-4B, with the first port 61 coupled to the intermediate tubing 18 and the side port 62 extending substantially perpendicular to the first port 61 and configured to be coupled to, e.g., the extension tubing 20. The near-patient access port 60 further includes the female luer connector 63.

Additionally, the integrated catheter configuration 400 includes a removable needle free connector 110, with the needle free connector 110 being configured to be removably couplable to the female luer connector 63 of the near-patient access port 60. Alternatively, in other embodiments, it is to be understood that the needle free connector 110 may be integrated (i.e., non-removable) with the near-patient access port 60. The needle free connector 110 may be utilized as a connection interface between the near-patient access port 60 and, e.g., a blood draw device such as blood draw device 200 described above with respect to FIG. 2.

Referring still to FIGS. 5A and 5B, the needle free connector 110 may also incorporate a stabilization platform 120. In this way, the stabilization platform 120 is associated with the needle free connector 110, not the near-patient access port 60. In some embodiments, stabilization platform 120 is formed separately from, and may be attached or coupled to, the needle free connector 110. However, in other embodiments, the stabilization platform 120 may be integrally formed with the needle free connector 110.

In some embodiments, stabilization platform 120 includes opposing stabilizing wings 121A, 121B, which may act provide improved securement and stability of the needle free connector 110 (as well as the near-patient access port 60) on the patient's skin. Such a configuration may improve the success of blood draw device compatibility and access with the integrated catheter, as well as reduce the risk of catheter and/or blood draw device complications (such as, e.g., flow tube kinking, etc.) due to device manipulation during access with the integrated catheter. Additionally and/or alternatively, the stabilization platform 120 may help to avoid patient skin irritation due to movement of the needle free connector 110.

Furthermore, because the needle free connector 110 may be removable from the near-patient access port 60, flushing of the near-patient access port 60 via, e.g., the medical component 36 at the end of the extension tubing 20 may be improved.

Stabilization platform 120 may be fully rigid, rigid with some flexibility, semi-rigid, semi-rigid with one or more flexibility hinges, soft, or soft with flexibility features. Additionally, in some embodiments, stabilization platform 120 may be angled and the female luer connector 63 and/or the needle free connector 110 may be raised to provide a substantially unrestricted pathway for advancement of the flexible flow tube of the blood draw device. Additionally, the stabilization platform 120 and/or stabilizing wings 121A, 121B may have a substantially flat bottom, a curved bottom, or a partially curved bottom.

As noted above, in some embodiments, the stabilization platform 120 may be formed separately from the needle free connector 110, and may be attached, bonded, and/or coupled to the needle free connector 110 via any appropriate method. Alternatively, the stabilization platform 120 may be integrally molded or formed as part of the needle free connector 110.

In each of the embodiments described above with respect to FIGS. 3A-5B, the near-patient access port is configured as a dual port adapter, with a side port couplable to extension tubing and/or a medical component. However, in accordance with other aspects of the present disclosure, the near-patient access port may be configured as a single port adapter. For example, referring to FIG. 6, an integrated catheter configuration 500 in accordance with another aspect of the present disclosure is shown. The integrated catheter configuration 500 includes a near-patient access port 140 configured as a single port adapter, with a port 141 coupled to the intermediate tubing 18 on a first end and a female luer connector 142 on a second end, with the female luer connector 142 configured to be couplable to, e.g., a removable needle free connector (NFC), a non-stabilized t-extension set, etc. The needle free connector (not shown) and/or the non-stabilized t-extension set (now shown) may be utilized as a connection interface between the near-patient access port 140 and, e.g., a blood draw device such as blood draw device 200 described above with respect to FIG. 2.

Figure 6:
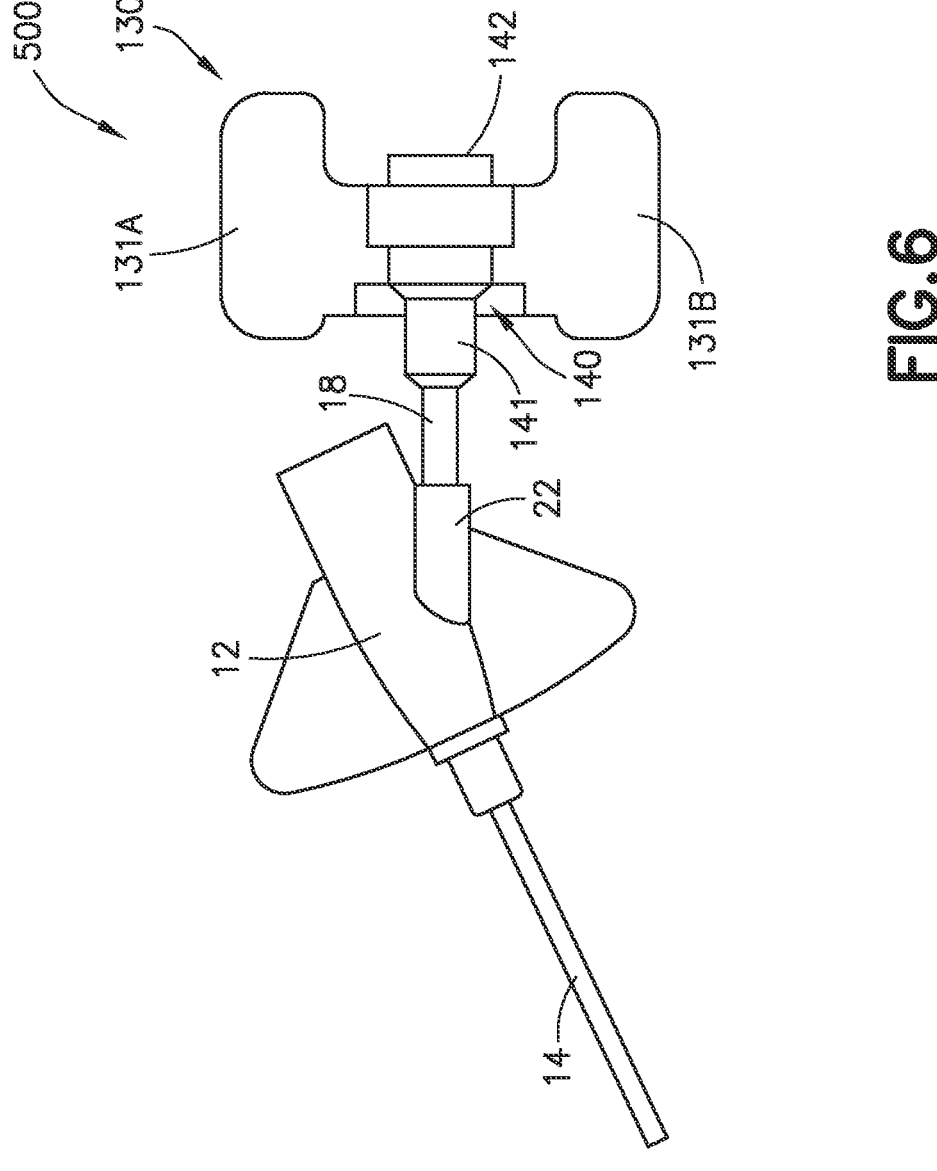
FIG. 6 is a top plan view of an integrated catheter configuration in an assembled configuration in accordance with another aspect of the present disclosure.

Referring still to FIG. 6, the integrated catheter configuration 500 also includes a stabilization platform 130. In some embodiments, stabilization platform 130 is formed separately from, and may be attached or coupled to, the near-patient access port 140. However, in other embodiments, the stabilization platform 130 may be integrally formed with the near-patient access port 140. In some embodiments, stabilization platform 130 includes opposing stabilizing wings 131A, 131B, which may act provide improved securement and stability of the near-patient access port 140 on the patient's skin. Such a configuration may improve the success of blood draw device compatibility and access with the integrated catheter, as well as reduce the risk of catheter and/or blood draw device complications (such as, e.g., flow tube kinking, etc.) due to device manipulation during access with the integrated catheter. Additionally and/or alternatively, the stabilization platform 130 may help to avoid patient skin irritation due to movement of the near-patient access port 140.

Stabilization platform 130 may be fully rigid, rigid with some flexibility, semi-rigid, semi-rigid with one or more flexibility hinges, soft, or soft with flexibility features. Additionally, in some embodiments, stabilization platform 130 may be angled and the female luer connector 142, the needle free connector (not shown), and/or the t-extension set (not shown) may be raised to provide a substantially unrestricted pathway for advancement of the flexible flow tube of the blood draw device. Additionally, the stabilization platform 130 and/or stabilizing wings 131A, 131B may have a substantially flat bottom, a curved bottom, or a partially curved bottom. The stabilization platform 130 may be formed separately from the near-patient access port 140, and may be attached, bonded, and/or coupled to the near-patient access port 140 via any appropriate method. Alternatively, the stabilization platform 130 may be integrally molded or formed as part of the near-patient access port 140.

Figure 7A:
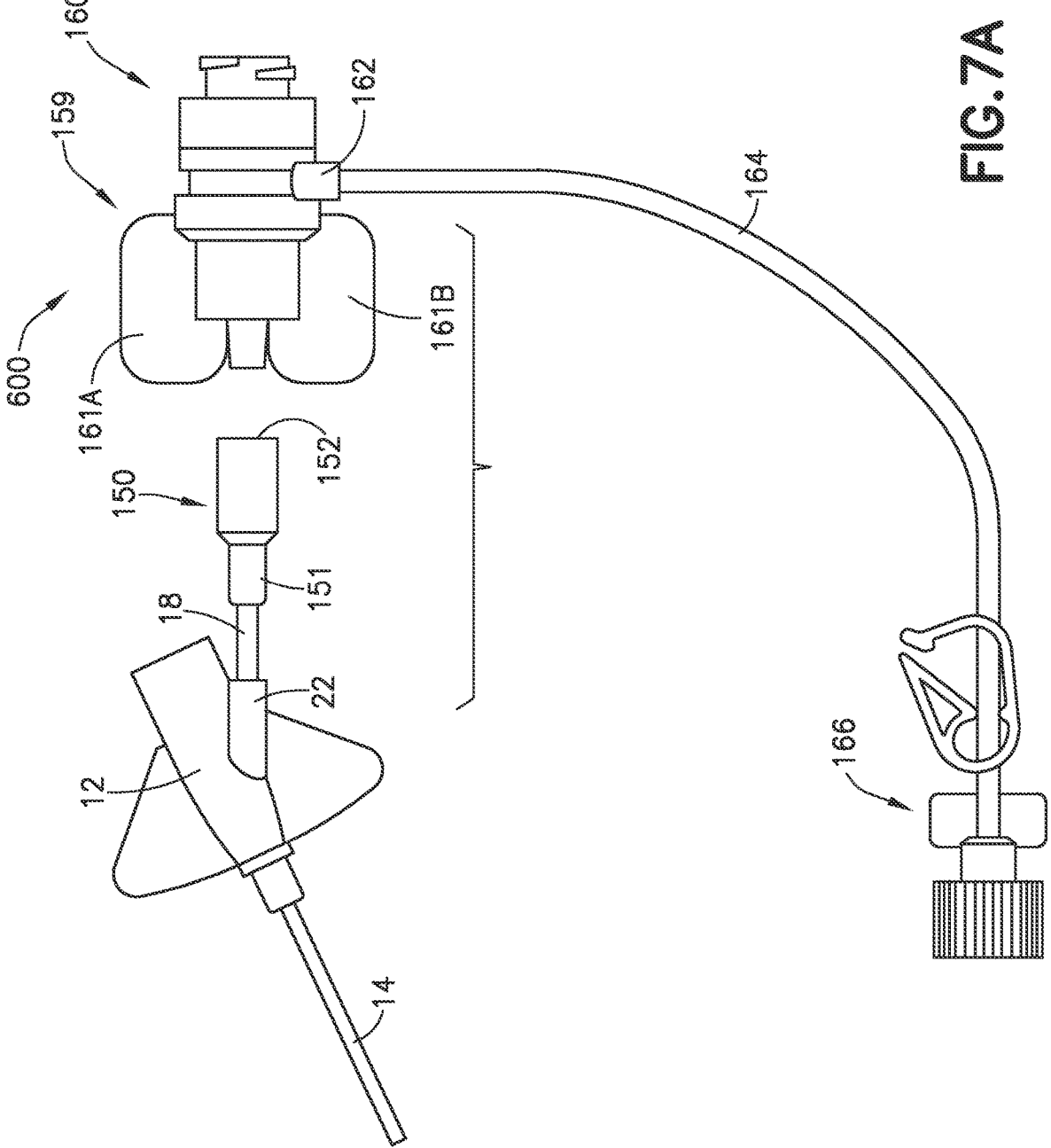
FIG. 7A is a top plan view of an integrated catheter configuration in a partially disassembled configuration in accordance with another aspect of the present disclosure.
Figure 7B:
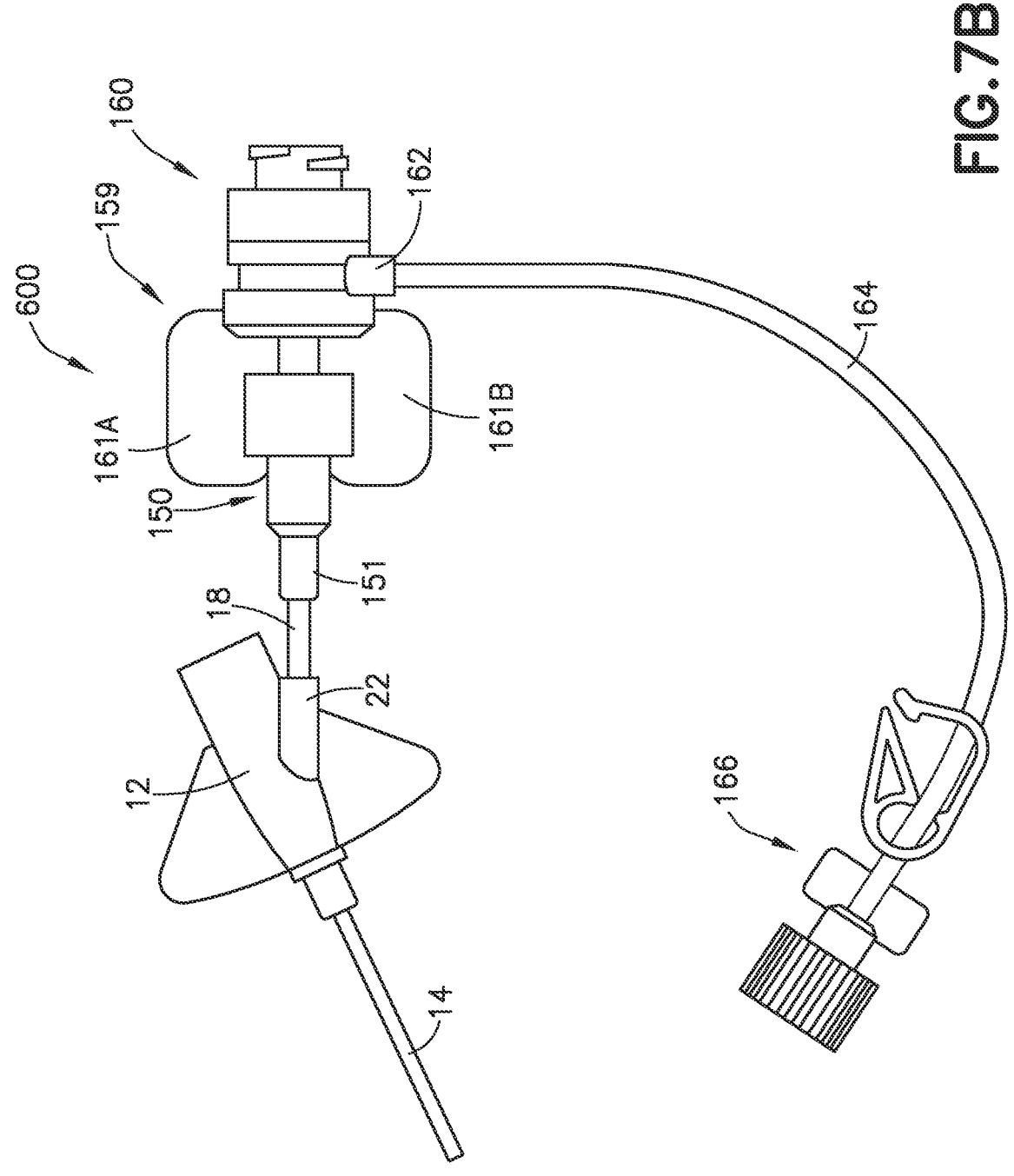
FIG. 7B is a top plan view of the integrated catheter configuration of FIG. 7A in an assembled configuration.

Referring now to FIGS. 7A and 7B, an integrated catheter configuration 600 in accordance with another aspect of the present disclosure is shown. Similar to integrated catheter configuration 500 described above with respect to FIG. 6, the integrated catheter configuration 600 includes a near-patient access port 150 configured as a single port adapter, with a port 151 coupled to the intermediate tubing 18 on a first end and a female luer connector 152 on a second end. However, unlike integrated catheter configuration 500, which included a stabilization platform 130 integrated with (or coupled to) the near-patient access port 140, the integrated catheter configuration 600 of FIGS. 7A and 7B includes a removable t-extension set 160, wherein the t-extension set 160 incorporates a stabilization platform 159. In the embodiment shown in FIGS. 7A and 7B, the t-extension set 160 is configured as a needle free connector removably couplable to the female luer connector 152 of the near-patient access port 150. The t-extension set 160 includes a side port 162 couplable to extension tubing 164, with the extension tubing 164 couplable to a medical component 166, such as, e.g., a vent plug. Alternatively, in other embodiments, it is to be understood that the t-extension set 160 may be integrated (i.e., non-removable) with the near-patient access port 150. Furthermore, it is to be understood that t-extension set 160 is not limited to a t-adapter configuration, and may instead be formed as a y-adapter (i.e., a 30°-150° adapter). The t-extension set 160 may be utilized as a connection interface between the near-patient access port 150 and, e.g., a blood draw device such as blood draw device 200 described above with respect to FIG. 2.

As noted above, the stabilization platform 159 is associated with the t-extension set 160, not the near-patient access port 150. In some embodiments, stabilization platform 159 is formed separately from, and may be attached or coupled to, the t-extension set 160. However, in other embodiments, the stabilization platform 159 may be integrally formed with the t-extension set 160. In some embodiments, stabilization platform 159 includes opposing stabilizing wings 161A, 161B, which may act provide improved securement and stability of the t-extension set 160 (as well as the near-patient access port 150) on the patient's skin. Such a configuration may improve the success of blood draw device compatibility and access with the integrated catheter, as well as reduce the risk of catheter and/or blood draw device complications (such as, e.g., flow tube kinking, etc.) due to device manipulation during access with the integrated catheter. Additionally and/or alternatively, the stabilization platform 159 may help to avoid patient skin irritation due to movement of the t-extension set 160.

Stabilization platform 159 may be fully rigid, rigid with some flexibility, semi-rigid, semi-rigid with one or more flexibility hinges, soft, or soft with flexibility features. Additionally, in some embodiments, stabilization platform 159 may be angled and the female luer connector 152 and/or the t-extension set 160 may be raised to provide a substantially unrestricted pathway for advancement of the flexible flow tube of the blood draw device. Additionally, the stabilization platform 159 and/or stabilizing wings 161A, 161B may have a substantially flat bottom, a curved bottom, or a partially curved bottom.

As noted above, in some embodiments, the stabilization platform 159 may be formed separately from the t-extension set 160, and may be attached, bonded, and/or coupled to the t-extension set 160 via any appropriate method. Alternatively, the stabilization platform 159 may be integrally molded or formed as part of the t-extension set 160.

Figure 8:
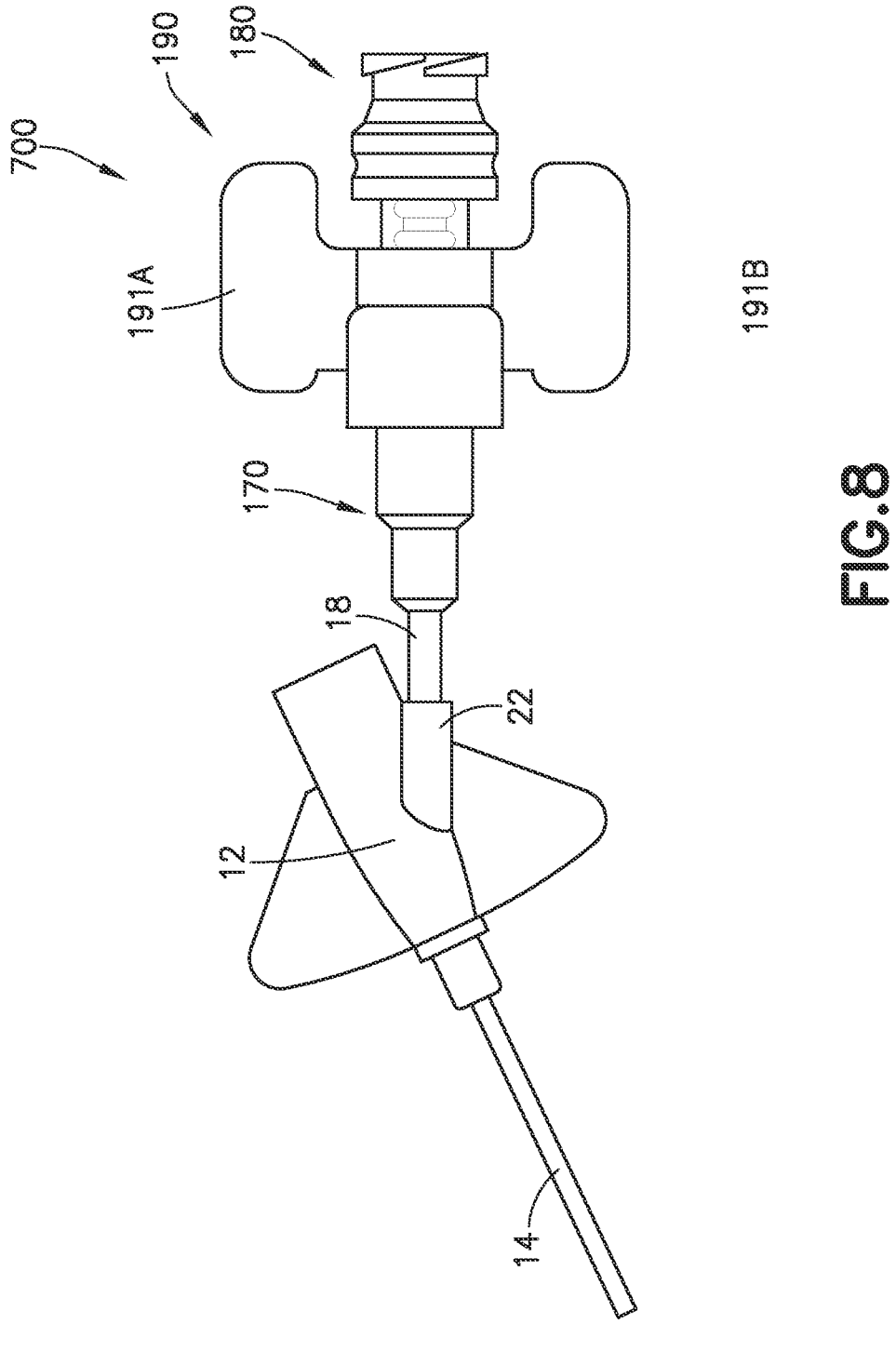
FIG. 8 is a top plan view of an integrated catheter configuration in an assembled configuration in accordance with another aspect of the present disclosure.

Referring now to FIG. 8, an integrated catheter configuration 700 in accordance with another aspect of the present disclosure is shown. Similar to integrated catheter configurations 500 and 600 described above with respect to FIGS. 6-7B, respectively, the integrated catheter configuration 700 includes a near-patient access port 170 configured as a single port adapter, with a port coupled to the intermediate tubing 18 on a first end and a female luer connector on a second end.

Additionally, the integrated catheter configuration 700 includes a removable needle free connector 180, with the needle free connector 180 being configured to be removably couplable to the female luer connector of the single port near-patient access port 170. Alternatively, in other embodiments, it is to be understood that the needle free connector 180 may be integrated (i.e., non-removable) with the near-patient access port 170. The needle free connector 180 may be utilized as a connection interface between the near-patient access port 170 and, e.g., a blood draw device such as blood draw device 200 described above with respect to FIG. 2.

The needle free connector 180 may also incorporate a stabilization platform 190. In this way, the stabilization platform 190 is associated with the needle free connector 180, not the near-patient access port 170. In some embodiments, stabilization platform 190 is formed separately from, and may be attached or coupled to, the needle free connector 180. However, in other embodiments, the stabilization platform 190 may be integrally formed with the needle free connector 180.

In some embodiments, stabilization platform 190 includes opposing stabilizing wings 191A, 191B, which may act provide improved securement and stability of the needle free connector 180 (as well as the near-patient access port 170) on the patient's skin. Such a configuration may improve the success of blood draw device compatibility and access with the integrated catheter, as well as reduce the risk of catheter and/or blood draw device complications (such as, e.g., flow tube kinking, etc.) due to device manipulation during access with the integrated catheter. Additionally and/or alternatively, the stabilization platform 190 may help to avoid patient skin irritation due to movement of the needle free connector 180. Stabilization platform 190 may be fully rigid, rigid with some flexibility, semi-rigid, semi-rigid with one or more flexibility hinges, soft, or soft with flexibility features. Additionally, in some embodiments, stabilization platform 190 may be angled and the female luer connector of the near-patient access port 170 and/or the needle free connector 180 may be raised to provide a substantially unrestricted pathway for advancement of the flexible flow tube of the blood draw device. Additionally, the stabilization platform 190 and/or stabilizing wings 191A, 191B may have a substantially flat bottom, a curved bottom, or a partially curved bottom.

As noted above, in some embodiments, the stabilization platform 190 may be formed separately from the needle free connector 180, and may be attached, bonded, and/or coupled to the needle free connector 180 via any appropriate method. Alternatively, the stabilization platform 190 may be integrally molded or formed as part of the needle free connector 180.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An integrated catheter comprising:
   a catheter adapter comprising a catheter and an inlet, the catheter configured to be inserted into a patient's vasculature;
   a near-patient access port having a first port at a first end and a female luer connector at a second end;
   intermediate tubing extending between the inlet of the catheter adapter and the first port of the near-patient access port;
   a needle free connector removably couplable to the female luer connector of the near-patient access port; and
   a stabilization platform configured to stabilize at least the near-patient access port on a patient's skin, wherein the stabilization platform is coupled to or integrally formed with the needle free connector.

2. The integrated catheter of claim 1, wherein the near-patient access port further comprises a side port extending therefrom.

3. The integrated catheter of claim 2, wherein the side port extends 90° relative to an axis of the first port and the female luer connector of the near-patient access port.

4. The integrated catheter of claim 2, further comprising extension tubing extending from the side port of the near-patient access port.

5. The integrated catheter of claim 4, further comprising a medical component positioned at an end of the extension tubing.

6. The integrated catheter of claim 1, wherein the stabilization platform is coupled to the needle free connector.

7. The integrated catheter of claim 1, wherein the stabilization platform is integrally formed with the needle free connector.

8. The integrated catheter of claim 1, wherein the needle free connector comprises a t-extension set removably couplable to the female luer connector of the near-patient access port.

9. The integrated catheter of claim 8, wherein the t-extension set comprises a side port coupled to a second extension tube, wherein the second extension tube is coupled to a second medical component.

10. The integrated catheter of claim 8, wherein the stabilization platform is coupled to the t-extension set.

11. The integrated catheter of claim 8, wherein the stabilization platform is integrally formed with the t-extension set.

12. The integrated catheter of claim 1, wherein the stabilization platform comprises opposing first and second stabilizing wings.

13. An integrated catheter comprising:

a catheter adapter comprising a catheter and an inlet, the catheter configured to be inserted into a patient's vasculature;

a near-patient access port having a first port at a first end and a female luer connector at a second end;

intermediate tubing extending between the inlet of the catheter adapter and the first port of the near-patient access port; and a stabilization platform configured to stabilize at least the near-patient access port on a patient's skin, wherein the stabilization platform is positioned on the near-patient access port, with the stabilization platform formed separate from and connected to the near-patient access port or formed integrally with the near-patient access port.

14. An integrated catheter comprising:

a catheter adapter comprising a catheter and an inlet, the catheter configured to be inserted into a patient's vasculature;

a near-patient access port having a first port at a first end and a female luer connector at a second end;

intermediate tubing extending between the inlet of the catheter adapter and the first port of the near-patient access port;

a needle free connector coupled to the female luer connector of the near-patient access port, wherein the needle free connector is removably couplable to the female luer connector; and a stabilization platform configured to stabilize at least the needle free connector on a patient's skin, wherein the stabilization platform is positioned on the needle free connector.

15. The integrated catheter of claim 14, wherein the needle free connector and the stabilization platform are removable from the female luer connector of the near-patient access port.

* * * * *